United States Patent [19]

Dunn et al.

[11] Patent Number: 4,959,066
[45] Date of Patent: Sep. 25, 1990

[54] FEMORAL OSTEOTOMY GUIDE ASSEMBLY

[75] Inventors: Harold K. Dunn, Salt Lake City, Utah; Mark A. Lazzeri; Jeffrey M. Ondrla, both of Warsaw, Ind.

[73] Assignee: Zimmer, Inc., Warsaw, Ind.

[21] Appl. No.: 315,101

[22] Filed: Feb. 24, 1989

[51] Int. Cl.$^5$ .............................................. A61B 17/56
[52] U.S. Cl. ........................................ 606/89; 606/87
[58] Field of Search ...... 128/92 VY, 92 VV, 92 VW, 128/92 VD, 92 VL; 411/400, 388, 389; 606/87, 89

[56] References Cited

U.S. PATENT DOCUMENTS

| | | | |
|---|---|---|---|
| D. 282,277 | 1/1986 | Kenna | D24/26 |
| 3,815,590 | 6/1974 | Deyerle | 128/92 EB |
| 3,893,362 | 7/1975 | Schneider et al. | 83/763 |
| 4,335,715 | 6/1982 | Kirkley | 128/92 EB |
| 4,409,973 | 10/1983 | Neufeld | 128/92 E |
| 4,621,630 | 11/1986 | Kenna | 128/92 VD |
| 4,703,751 | 11/1987 | Pohl | 128/92 VY |
| 4,736,737 | 4/1988 | Fargie et al. | 128/92 VY |
| 4,893,619 | 1/1990 | Dale et al. | 606/87 |

FOREIGN PATENT DOCUMENTS 2456506  5/1980  France .

OTHER PUBLICATIONS

The Howmedica Universal Total Knee Instrument System, undated.
R.M.C. Total Knee System, 1978.
Osteonics, Corp. Literature for Femoral Neck Resection Guide—No date available.
Howmedica, Inc.—Literature for Neck Cutting Guide for PCA Hip—No date available.
Bias Total Hip System Surgical Technique—Gustilo/-Kyle—Hennepin County Medical Center—1986—pp. 6, 7, 9, 10.
Harris Precoat Hip Prosthesis Surgical Technique—Zimmer, Inc.—1984—pp. 9-11.
Harris/Galante Porous Hip Prosthesis Surgical Technique—Zimmer, Inc.—1984—pp. 4, 5, 13, 14.
Catalog pages from Zimmer, Inc. Catalog—1987—pp. A-22, A-27, A-40, A-41: A-22—Harris Precoat Femoral Neck Osteotomy Guide; A-27—Harris/Galante Femoral Neck Osteotomy Guide; A-40—Bias Hip Revision Osteotomy Guide Set; A-40—Bias Hip Primary Osteotomy Guide Set; A-41—Bias Hip T-Handle and Tapered Reamer.
Protek AG Literature—Preoperative Planning of a Total Hip Replacement—M. E. Muller—1987.

*Primary Examiner*—Robert A. Hafer
*Assistant Examiner*—Kevin G. Rooney
*Attorney, Agent, or Firm*—Margaret L. Geringer

[57] ABSTRACT

An osteotomy guide assembly for femoral neck osteotomy includes a saddle locator assembly and a saw guide attachment. The saddle locator assembly includes a barrel-shaped locating device that locates the saddle region of the proximal femur. The barrel further includes a transverse support bar extending from the barrel. The barrel is positioned over an intramedullary shaft which is temporarily positioned in and extends from the medullary canal of the femur. A saw guide is used in conjunction with the saddle locator assembly. The saw guide is attached to the support bar by a single locking means which provides for positional adjustment of the saw guide relative to the support bar in two directions, including adjustment in the anterior-posterior direction along the transverse support bar and axially along the femur via a post which extends from the saw guide.

31 Claims, 3 Drawing Sheets

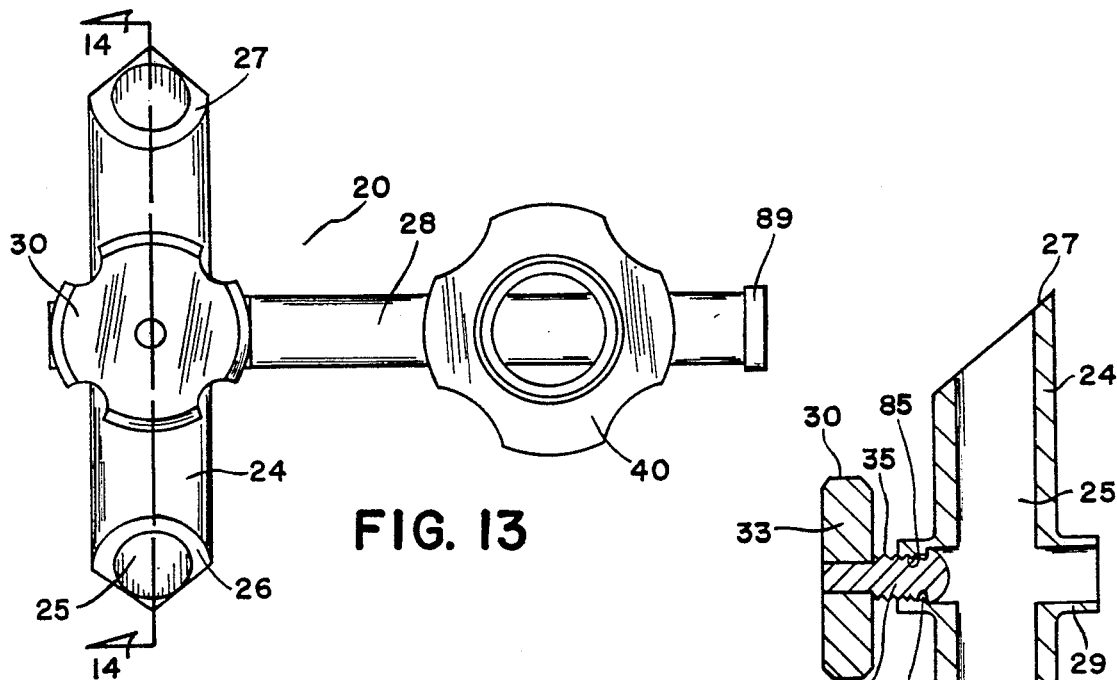
FIG. 13
FIG. 14
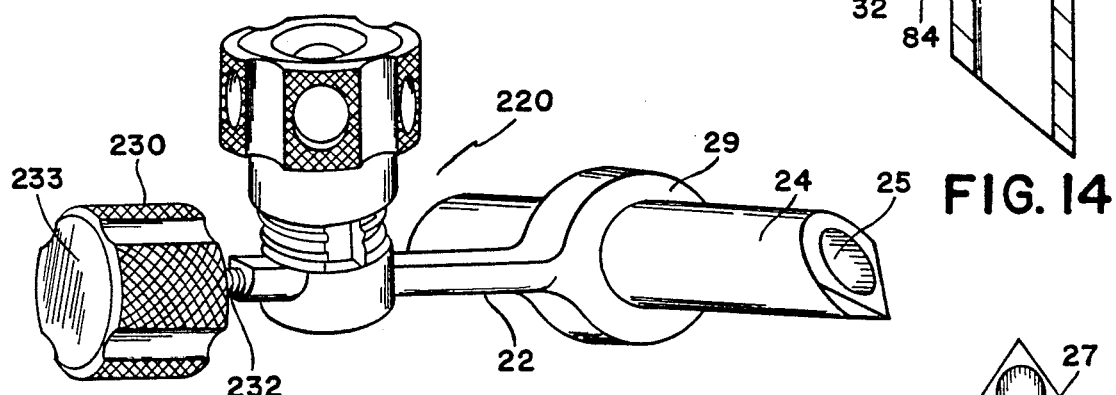
FIG. 15
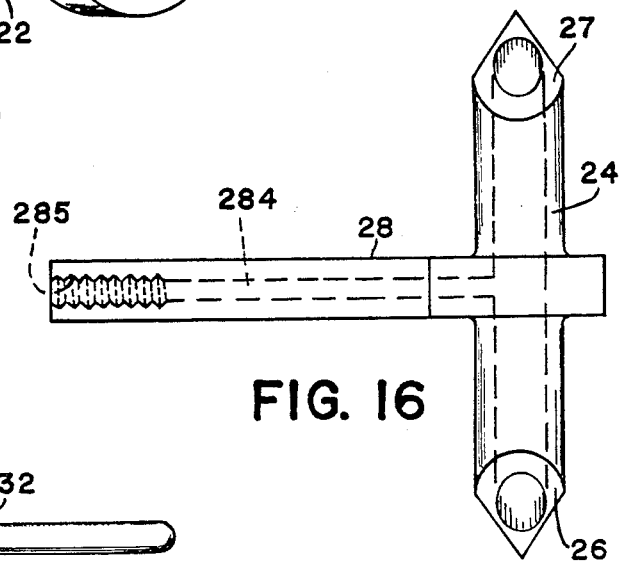
FIG. 16
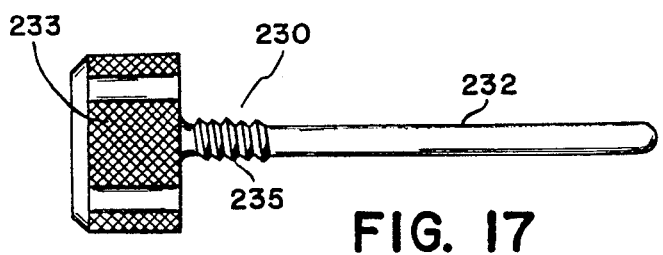
FIG. 17

FEMORAL OSTEOTOMY GUIDE ASSEMBLY

BACKGROUND OF THE INVENTION

The present invention relates to femoral neck osteotomy, and more particularly to an osteotomy guide assembly and method for cutting a femoral neck at a desired angle in relation to the long shaft of the femur.

The femur 2 (See FIG. 5) articulates with the acetabulum by a rounded head 6 connected with the shaft 9 of the bone by an oblique neck 7. A pair of eminences called trochanters are located at the junction of the neck and shaft for attachment of muscle. The greater trochanter 4 is situated at the outer part of the upper (or proximal) end of the shaft at its junction with the neck, and the lesser trochanter 5 is at the lower back part of the junction of the shaft and neck. The upper portion of the neck between the greater trochanter and the head is referred to as the saddle portion 8.

Hip arthroplasty typically requires cutting off the head and neck of the femur (such as along line "L" indicated in FIG. 5). The precision of this cut is important to the proper placement of the hip prosthesis implant which will subsequently be installed into the femur. Various types of osteotomy or cutting guides have been utilized for cutting off the head and neck of the femur.

U.S. Pat. No. 4,621,630 to Kenna discloses a guide for femoral neck osteotomy comprising a longitudinal rod having attaching structure at the lower end thereof for securing the rod to a femur at the greater trochanter. A transversely extending support arm is secured to the rod adjacent the lower end thereof, and a guide bar is connected to the support arm. The guide bar has at least one elongate planar surface disposed at an angle to the axis of the rod. A cutting instrument is used in engagement with the planar surface to guide the cutting instrument in cutting the femoral bone at the desired angle. The guide bar is slideable along the support arm toward or away from the longitudinal rod for transverse positional adjustment, but is prevented from rotating relative to the support arm. U.S. Design Pat. No. 282,277 to Kenna also illustrates the ornamental features for a guide for femoral neck osteotomy which corresponds to the guide shown in U.S. Pat. No. 4,621,630.

A Femoral Neck Resection Guide, illustrated in literature for Osteonics Corp., discloses a guide assembly which fits over a reamer shaft which has been used to ream the medullary canal. The assembly includes a block having a hole therethrough for fitting over the portion of the reamer shaft extending from the femur. A resection cutting or saw guide having an angled cutting surface is aligned so that the cutting surface is parallel to the intended cutting plane on the bone. This is done by adjusting the axial position of the guide in relation to the elongated reamer shaft. The guide is anchored to the shaft in the desired position by tightening a locking screw. The cut in the bone is made up to the approximate depth of the intramedullary reamer. The reamer and guide assembly are removed and the resection of the neck is completed.

A Femoral Neck Cutting Guide is illustrated in literature for Howmedica, Inc. for the PCA Hip. The cutting guide is secured to the greater trochanter by impacting pins protruding from an elongated shaft into the bone of the greater trochanter. A transverse bar extends from the shaft. A cutting bar is attached to the shaft. Two different locking mechanisms are utilized to locate the position of the cutting bar to the transverse bar. One locking screw adjusts the transverse position of the cutting bar along the transverse bar. A second separate locking mechanism adjusts the axial position of the cutting bar in relation to the transverse bar, and thus axially along the longitudinal direction of the femur.

A Surgical Technique, by Gustilo and Kyle, for the BIAS Total Hip System (©1986 Hennepin County Medical Center), discloses an osteotomy guide which has a barrel with a fixed transverse bar extending therefrom and a fixed cutting guide attached thereto. The barrel fits over the protruding end of an intramedullary reamer. The cutting guide has a flat shape which corresponds to an anterior-posterior view of the neck portion of a hip prosthesis implant with a cutting slot partially extending into the medial side of the plate. A plurality of holes is provided on the neck portion to aid in alignment for hip stem prostheses of varying neck lengths. Clear acrylic templates with an outline of the stem to be implanted may be used in conjunction with the osteotomy guide to aid in positioning of the guide. This guide does not provide for adjustment of the cutting guide plate relative to the transverse bar since it is in a fixed relation thereto.

The Surgical Technique for the Harris Precoat Hip Prosthesis (©1984 Zimmer, Inc.) discloses a neck osteotomy guide that is a flat piece of metal cut in the outline of a flag and depending stem. It includes positioning cutouts or holes to aid in alignment for hip stem prostheses of varying neck lengths. The guide is superimposed over the femoral shaft with the posterior surface of the flag abutting the femoral head and with its stem in line with the midline of the medullary canal. The inferior margin of the flag portion of the neck osteotomy guide indicates the position for the osteotomy. This guide is not physically attached to the femur.

The Surgical Technique for the Harris/Galante Porous Hip Prosthesis (©1984 Zimmer, Inc.) discloses a neck osteotomy guide that is a flat piece of metal cut in a shape corresponding to the anterior-posterior view the hip prosthesis stem to be implanted, having a neck and depending stem portion. A cutting slot is provided between the neck and stem portion which partially extends into the medial side of the plate. The neck and depending stem portion are connected along the lateral side of the plate. A reference scale is provided along the medial side of the plate. The plate is superimposed on top of the femur and is not physically attached to the femur. Clear acrylic templates with an outline of the stem to be implanted may be used in conjunction with the osteotomy guide to aid in positioning of the guide. The templates are typically superimposed over a patient's X ray during preoperative planning. The template also includes a medial scale which can be used to reference positioning with the corresponding scale on the osteotomy guide during surgery.

OBJECTS OF THE INVENTION

It is an object of the present invention to provide a femoral neck osteotomy guide assembly which is attached to the femur for accurate determination of the neck cutting level and which provides for adjustment of the saw or cutting guide with reference to the femur in both the transverse (anterior-posterior) direction and axially along the femur.

It is a further object of the invention to have these two adjustment directions for the saw guide to be adjustable and then secured along a transverse support bar via a single locking mechanism.

Another object of the invention is to provide an osteotomy guide assembly which locates off of the saddle portion of the femur.

A still further object of the invention is to provide an osteotomy guide that is versatile, simple to manufacture and use, and also one which is easily adjustable.

SUMMARY OF THE INVENTION

The present invention provides an osteotomy guide assembly for femoral neck osteotomy. The assembly includes a saddle locator assembly and a saw guide attachment. The saddle locator assembly includes a barrel-shaped locating device that locates the saddle region of the proximal femur. The saddle locator further includes a transverse support bar which extends from the barrel. The barrel is positioned over an intramedullary shaft which is temporarily positioned in and extends from the medullary canal of the femur. A saw guide is used in conjunction with the saddle locator assembly. The saw guide is attached to the support bar by a locking means which provides for positional adjustment of the saw guide relative to the support bar in two directions, including adjustment in the anterior-posterior direction along the transverse support bar and axially along the femur via a post which extends from the saw guide.

BRIEF DESCRIPTION OF THE DRAWINGS

These features and objects of the invention, as well as others, will become apparent to those skilled in the art by referring to the accompanying drawings:

FIG. 13 is side view of the saddle locator assembly of FIG. 8;

FIG. 14 is a cross-sectional view of the saddle locator assembly taken along lines 14—14 of FIG. 13;

FIG. 15 is an alternate embodiment of the saddle locator assembly;

FIG. 16 is a side view of the saddle locator of the assembly of FIG. 15; and

FIG. 17 is a side view of the barrel locking screw of the saddle locator assembly of FIG. 15.

DETAILED DESCRIPTION OF THE INVENTION

Figure 1:
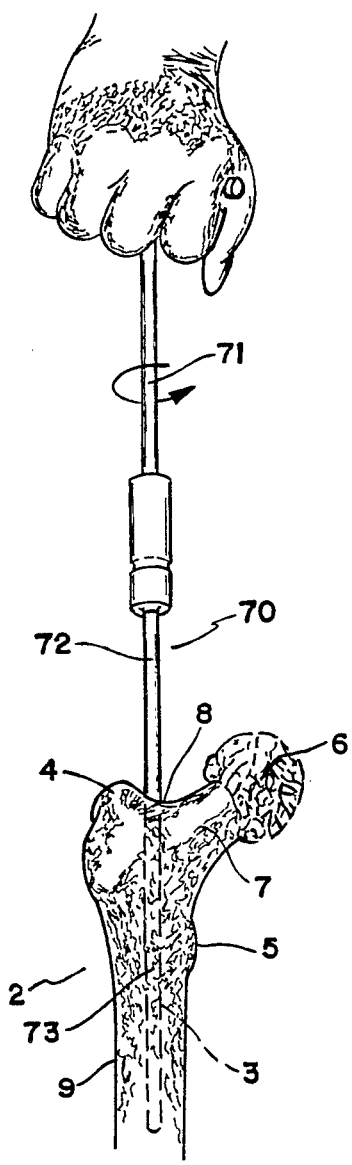
FIG. 1 is a front view of the proximal portion of a femur illustrating an intramedullary reamer being inserted into the femur.

FIGS. 2–4, 6, and 8–14 illustrate a particularly advantageous embodiment of a femoral osteotomy guide assembly 10 according to the present invention for performing a femoral neck osteotomy where the femoral head 6 and neck 7 are cut away from the shaft 9 of the proximal end of a femur 2.

The guide assembly 10 includes a saddle locator assembly 20, a saw guide 60 for attachment to the locator assembly 20, and an elongated intramedullary shaft 70 which may be interconnected with the locator assembly 20 to attach the locator assembly 20 to the femur 2. The intramedullary shaft 70 may be a shaft of a twist reamer that has been used to form a hole in the intramedullary canal 3 of the femur 2 as shown in FIG. 1, although any suitable elongated shaft positioned in the canal and extending therefrom could be utilized. The shaft 70 of the reamer may be inserted via a detachable T-handle 71 (as shown) or other suitable manual or power-inserting instrument. The T-handle 71 is removed leaving the distal taper portion 73 of the shaft 70 in the intramedullary canal 3 and the proximal end 72 of the shaft 70 protruding from the proximal end of the femur 2.

Figure 2:
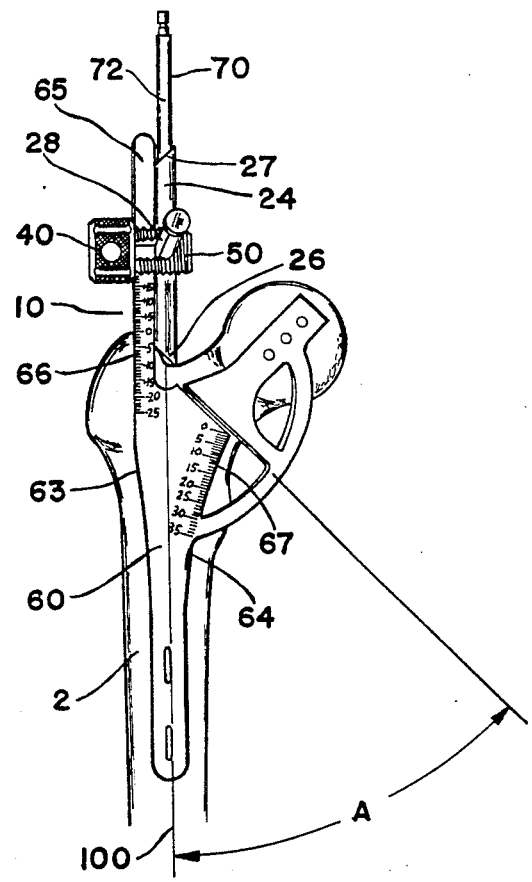
FIG. 2 is a front view of the osteotomy guide assembly of the present invention shown attached to a femur.
Figure 3:
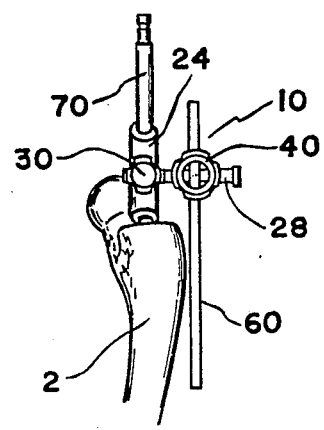
FIG. 3 is a lateral view of the invention of FIG. 2.
Figure 4:
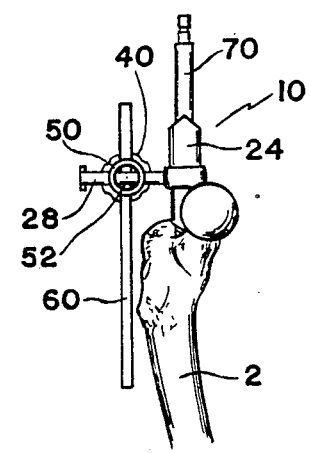
FIG. 4 is a medial view of the invention of FIG. 2.

The saddle locator assembly 20 includes a saddle locator 22, barrel locking screw 30, and a dual adjustment locking mechanism 15. The saddle locator 22 includes an elongated barrel 24 and a transverse support bar 28 extending therefrom. The barrel 24 includes a channel 25 therethrough enabling the barrel 24 to fit over the protruding end of shaft 70 for stabilizing and locating the barrel thereon. When the barrel 24 is located on the shaft 70 extending from the femur 2, the barrel is intended to rest on or locate the saddle portion 8 of the femur 2 as shown in FIG. 2.

The saw guide 60 is attachable to the support bar 28 by the dual adjustment locking mechanism 15. This locking mechanism 15 provides for positional adjustment of the saw guide 60 relative to the transverse support bar 28 in at least two different directions, including a first direction transversely along the support bar 28 and a second direction axially along the longitudinal direction of the femur 2. When adjusting the saw guide 60 transversely along the support bar 28, this provides positional adjustment in the anterior-posterior direction toward or away from the femur 2 (in a substantially horizontal direction along bar 28 as viewed in FIGS. 3 and 4). When adjusting the saw guide 60 axially in relation to the support bar 28, this provides positional adjustment axially along the longitudinal direction of the femur 2 (in a substantially vertical, up and down direction as viewed in FIGS. 2–4).

The saw guide 60 includes an upwardly extending post 65 which is attached to the support bar 28 by the dual adjustment locking mechanism 15. This locking mechanism 15 includes a stud 50 and a locking member 40. The stud 50 is slideable along the bar 28 and slideably accepts the post 65 of the saw guide 60. The locking member 40 can be selectively tightened onto the stud 50 to secure the position of the stud 50 along the bar 28 as well as secure the position of the post 65 of saw guide 60 in relation to the bar 28.

Figure 10:
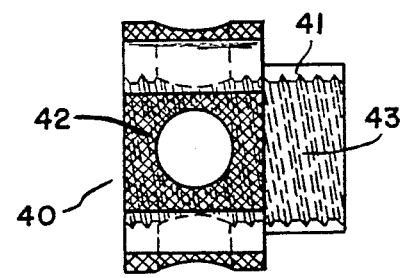
FIG. 10 is a top view of the dual adjustment locking screw of the saddle locator assembly of FIG. 9.
Figure 11:
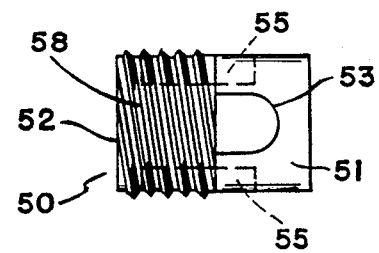
FIG. 11 is a side view of the dual adjustment locking stud of the saddle locator assembly of FIG. 9.
Figure 12:
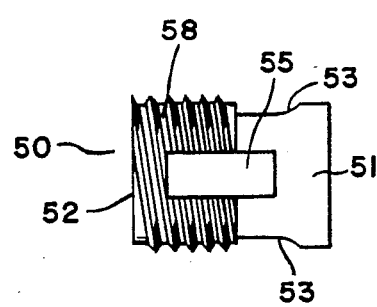
FIG. 12 is a top view of the stud of FIG. 11.

As shown in FIG. 10, the locking member 40 is a locking screw having a hollow shaft 41 and an enlarged gripping portion 42. The locking screw 40 includes an internal threaded portion 43 within the hollow shaft 41. The stud 50, as shown in FIGS. 11–12, includes an elongated shaft 51 having a hollow channel 52 throughout. The stud 50 includes corresponding external threads 58 to provide a threaded adjustment between the locking screw 40 and stud 50.

The stud 50 includes a first channel 53 therethrough for slideably accepting the support bar 28. Since the stud 50 is hollow, first channel 53 forms two oppositely located openings in stud 50. The stud 50 also includes a second channel 55 having a different orientation from the first channel 53. (As shown, channel 53 and channel 55 are substantially perpendicular to each other.) The second channel 55 is for slideably accepting the post 65 of saw guide 60. Again, since the stud 50 is hollow, second channel 55 forms two oppositely located openings in stud 50. The post 65 is positioned in channel 55 between support bar 28 and locking screw 40.

Figure 9:
FIG. 9 is a cross-sectional view of the saddle locator assembly taken along lines 9—9 of FIG. 8.

As shown in FIG. 9, bar 28 has a "D" shaped cross-section. The rounded portion of the "D" fits into a corresponding rounded end of channel 53 (the two openings which form channel 53). This fit prevents rotation of the stud relative to the bar 28. The post 65 has a box-shaped cross-section (cross-section not shown) which fits into the box-shaped channel 55. When the dual locking mechanism 15 is tightened to secure both the transverse and axial position of the saw guide 60 to the bar 28, these corresponding boxed shapes of the post 65 and channel 55 prevent twisting or rotation of the saw guide 60 relative to the osteotomy guide assembly 10.

Figure 8:
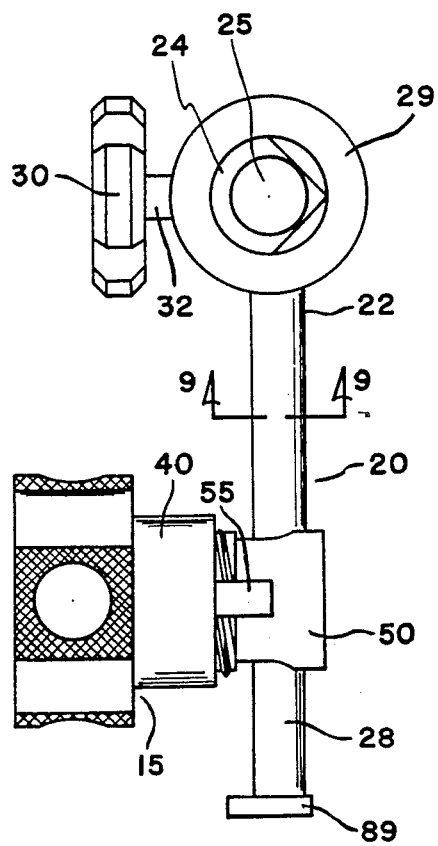
FIG. 8 is a top view of the saddle locator assembly of the invention of FIG. 2.

FIG. 8 shows enlarged stop 89 on bar 28 which may be welded or otherwise attached to bar 28 after stud 50 has been positioned on bar 28. Stop 89 prevents stud 50 from sliding off bar 28.

Figure 6:
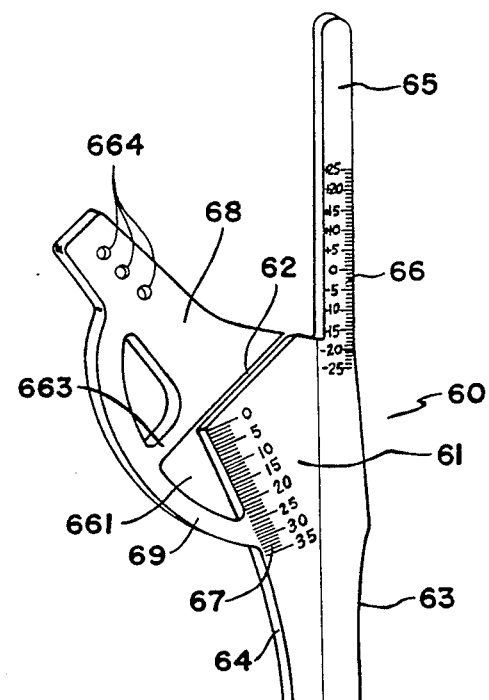
FIG. 6 is a perspective view of the saw guide of the osteotomy guide assembly of FIG. 2.

The saw guide 60 provides a surface or a slot 62 for aligning a suitable cutting instrument at a particular orientation against a femur 2. Although various saw guide devices which are attachable to the dual locking mechanism 15 may be utilized with the osteotomy guide assembly 10, FIG. 6 illustrates a particularly advantageous embodiment for a saw guide 60 in accordance with the present invention. Saw guide 60 of FIG. 6 provides a substantially flat plate having a shape which substantially corresponds to at least a portion of an anterior-posterior view of a suitable hip prosthesis. Accordingly, the shape could vary in keeping with the various corresponding shapes of femoral stem implants which may be implanted. The saw guide 60 includes a lateral side 63 and a medial side 64. The post 65 extends upwardly from the lateral side of the saw guide 60.

The saw guide 60 includes a first scale 66 for assisting the surgeon in determining the proper osteotomy level, and thus determining the relative position of the saw guide 60 to the femur 2. This first scale 66 is located along the lateral side 63 of the saw guide 60 and extends up into the post 65. This first scale 66 measures the osteotomy level (or the resultant position of the cutting surface or slot 62) from the center of the head 6. The center of the head 6 is generally considered to be horizontally aligned with the top surface of the greater trochanter 4. Many hip stem implants (not shown) are offered in multiple sizes and with varying neck lengths which affects the resulting position of the center of the head of the implant with respect to the femur 2 into which the implant will be installed.

Figure 7:
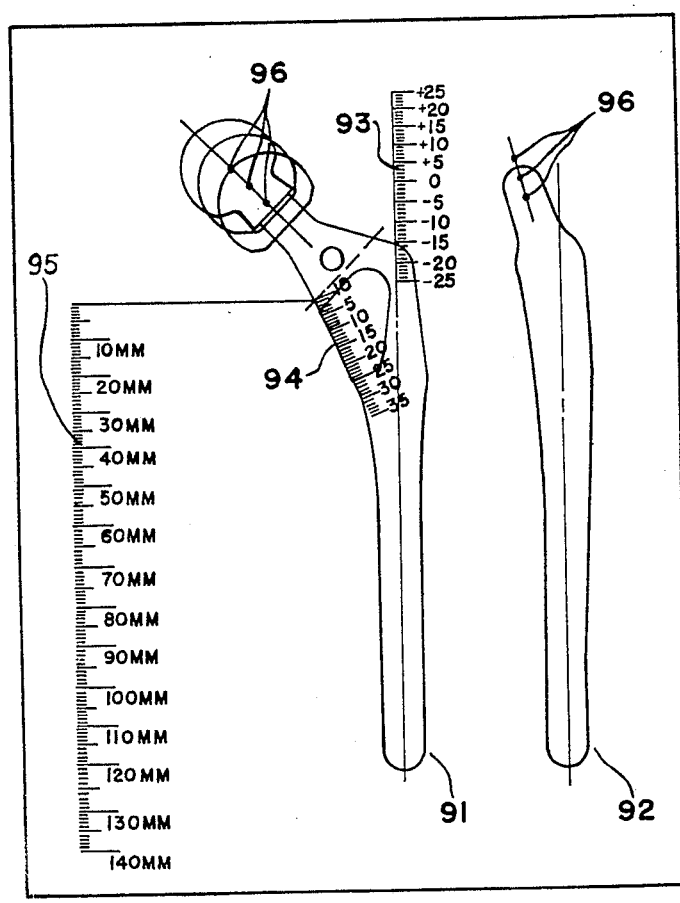
FIG. 7 is a template for use in conjunction with the osteotomy guide of FIG. 2.

This first scale 66 corresponds to a scale 93 on a template 90 as shown in FIG. 7. Template 90 is a thin clear acrylic sheet having an outline 91 of the anterior-posterior view of a hip implant and an outline 92 of the lateral view of the implant. Points 96 correspond to the center of the heads for femoral implants having varying neck lengths, short (S), medium (M), and long (L). Saw guide 60 also includes corresponding "S", "M", and "L" holes 664. The scale 66 on saw guide 60 and corresponding scale 93 on template 90 are oriented s that the "0" point on the scale aligns horizontally across from the medium "M" position, although other numerical arrangements or orientations of the scale could be utilized. The templates 90 may be used by the surgeon preoperatively by superimposing a template over the patient's X ray to determine the proper size implant that best fits the patient. Multiple templates are available to correspond to the multiple sizes of femoral implants that are available for a given or desired hip implant design. The surgeon can then take the template for the chosen size implant and use the scale 66 as a guide for determining the corresponding level of osteotomy during surgery via the osteotomy guide assembly 10.

The saw guide 60 may also include a second scale 67 located along the medial side 64 of saw guide 60. This second scale 67 measures the osteotomy level relative to the lesser trochanter 5. A corresponding medial scale 94 is also shown on template 90. The provision of both the first and second scales 66 and 67 allows the surgeon the option of choosing whether to measure the osteotomy level from the center of the femoral head (scale 66) or from the lesser trochanter (scale 67).

A sizing scale 95 is also included on template 90. This scale 95 denotes relative sizing, since the outlines on the template are enlarged by twenty percent from actual size, to account for the scaled enlargement that occurs with X rays (since the template is placed over the patient's X ray). The scales shown are marked in millimeters.

Figure 5:
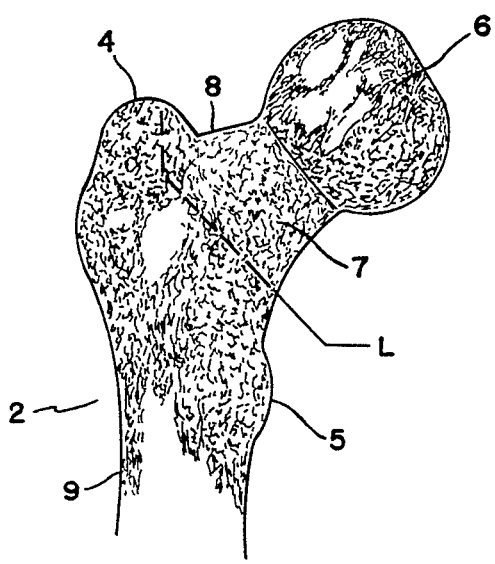
FIG. 5 is a front view of the proximal portion of a femur showing a typical or desired cutting line "L" for a femoral neck osteotomy.

The saw guide 60 includes a main body portion 61 and a further neck portion 68 separated from the main body portion 61 by cutting slot 62. The neck portion 68 is attached to the main body position 61 by a connecting leg 69 which extends outwardly from the medial side of the plate to interconnect the main body 61 and neck portion 68. The holes 664 are located in neck portion 68 and are utilized as a positioning means for corresponding with the center of the head of the femur or center of the head of the implant to be installed in the femur. The connecting leg 69 forms an opening 661 between the leg 69 and main body 61 which opens into the cutting slot 62. A cutting instrument (not shown) can be inserted from the opening 661 and into the slot 62. A cut in the femur can be made which aligns with slot 62 which guides the cutting instrument. The cut is continued throughout the length of the slot 62, and thus to about the longitudinal position of the reamer or shaft 70. At this point, osteotomy guide assembly 10, including shaft 70, would be removed from the canal 3 of femur 2. The resection of the neck is then completed generally as shown along line "L" of FIG. 5. The vertical or axial portion of the cut is made at the medial border of the greater trochanter to connect with the angled portion of the cut after assembly 10 has been removed from femur 2. The angled portion of the cut, as well as the angle of slot 62, may be at a suitable angle "A" to the longitudinal axis 100 of femur 2 as shown in FIG. 2. An appropriate angle "A" would be 45° although it may vary in accordance with the design of the implant being utilized.

It is also noted that a plurality of saw guides 60 may be provided having varying shapes and sizes which each corresponds to the plurality of shapes and sizes of implants available. The desired size saw guide 60 may then be selectively attached to the osteotomy guide assembly 10.

Regarding the barrel 24 of saddle locator 22 which fits over shaft 70, it is noted that shaft 70 is substantially axially aligned with the longitudinal direction of femur 2. Thus, the barrel 24, when positioned over shaft 70, is also substantially axially aligned with the longitudinal direction of femur 2. The transverse support bar 28 extends substantially perpendicularly from barrel 24. The barrel 24 may include an enlarged central ring 29 thereabout from which support bar 28 extends.

The barrel 24 is slideable along shaft 70. The saddle locator assembly 20 further includes a barrel locking screw 30 to secure the barrel 24 to the protruding portion of shaft 70 to secure the axial position of the barrel 24 relative to shaft 70. The barrel locking screw 30 includes a locking shaft member 32 which is positioned in a locking channel 84 (as shown in FIG. 14) which extends through a side wall of the barrel 24. The locking shaft member 32 may be selectively positioned to protrude into the channel 25 of barrel 24, and thus into contact with shaft 70 when barrel 24 is positioned over shaft 70 to secure barrel 24 to shaft 70. The locking shaft member 32 may also be selectively withdrawn out of contact with shaft 70 to release the secured position of barrel 24 relative to shaft 70. The locking shaft member 32 includes threads 35 for engaging corresponding threads 85 in channel 84. The locking shaft member 32 also includes enlarged knob 33 to assist in selectively manipulating member 32.

FIGS. 15-17 illustrate an alternate embodiment for the saddle locator assembly 220 in which the locking channel 284 extends through a side wall of barrel 24 and further extends continuously throughout the length of bar 28. Channel 284 includes a threaded portion 285. The barrel locking screw 230 includes locking shaft member 232 with corresponding threads 235 for threaded engagement with channel 284. Locking shaft member 232 includes enlarged knob 233 to assist in selectively manipulating member 232.

The elongated barrel 24 in both embodiments of the saddle locator assembly 20 and 220 includes a first end 26 and second end 27. Both ends as shown are angled tips. One of the angled ends 26 (see FIG. 2) is intended to be positioned at the saddle portion 8 of femur 2 when barrel 24 is located on shaft 70. The tip 26 in contact with the femur 2 angles downwardly away from the greater trochanter 4 of femur 2. The angled tip 27 at the opposite end of barrel 24 is provided to enable either the first end 26 or second end 27 to be placed against the saddle portion 8 of femur 2 which allows for flexibility upon installation of barrel 24 on shaft 70.

The osteotomy guide assembly 10 can be adapted for use with various styles of hip implants. It is a versatile instrument that can be used for either an anterior or posterior surgical approach and also can be used for a left or right hip procedure. In addition, if a surgeon prefers or if a revision hip procedure is required (a procedure where an existing implant is removed and replaced by a new implant, thus the head and neck have already been removed), the saw guide 60 may be used without the rest of osteotomy guide assembly 10. In this case the saw guide 60 is manually positioned against the femur 2 to determine the level of osteotomy, or in the case of a revision, to make any necessary adjustments to the cut surface.

It is noted that any suitable materials may be utilized for the osteotomy guide assembly 10. One such material is stainless steel. Regarding manufacturing methods, any suitable methods may be utilized.

In utilizing the osteotomy guide assembly 10 of the present invention, a longitudinal hole is formed in the femur 2 from the proximal end thereof that is aligned with the medullary canal 3 of femur 2, as shown in FIG. 1. The T-handle 71, which was used to drive and rotate the reamer shaft 70, is then detached from the elongated reamer shaft 70 which is left in femur 2 so that a distal end 73 of shaft 70 extends into the hole in medullary canal 3 and so that a proximal end 72 of shaft 70 protrudes from the proximal end of femur 70.

Hollow barrel 24 is positioned over proximal end 72 of shaft 70. The appropriate size saw guide 60 is selected and positioned along support bar 28. The post 65 is inserted into channel 55 of stud 50 which is located on transverse bar 28. The stud 50 can be slid along bar 28 to locate the saw guide 60 in the desired transverse or anterior-posterior position in relation to the femur a nd the post 65 can be axially (vertically) adjusted to position the axial position of cutting slot 62 of saw guide 60 relative to femur 2. The dual adjustment locking mechanism 15 is then tightened to secure both this transverse and axial position with a single locking means (15) by tightening locking screw 40 of locking means 15. A cutting instrument is then guided along cutting slot 62 of saw guide 60 and thus against the femoral neck 7. The osteotomy guide assembly 10 is removed from the femur 2. The cutting off of the head and neck from femur 2 is then completed with the cutting instrument.

While this invention has been described and exemplified in terms of particularly advantageous embodiments, those skilled in the art can appreciate that modifications can be made without departing from the spirit and scope of this invention.

We claim:

1. An osteotomy guide assembly for femoral neck osteotomy comprising a means for attaching the assembly to the proximal portion of a femur, a transverse support bar extending from said attachment means and a saw guide means which is attached to the support bar by a single locking means, and wherein said single locking means provides for positional adjustment of the saw guide means relative to the support bar in at least two different linear directions.

2. The guide assembly of claim 1 wherein the saw guide means is comprised of a plurality of saw guide plates of varying shapes and sizes, and wherein one of said plurality of plates may be selectively attached to said osteotomy guide assembly.

3. The guide assembly of claim 1 wherein the at least two different linear directions include a first direction transversely along the support bar and a second direction axially along the longitudinal direction of the femur.

4. The guide assembly of claim 3 wherein the saw guide means includes an extending post and wherein said post is attached to the support bar by the single locking means.

5. The guide assembly of claim 4 wherein the single locking means includes a stud which is slideable along the bar and which also slideably accepts the post of the saw guide and includes a locking member which can be selectively tightened onto the stud to secure the position of the stud along the bar as well as secure the position of the post in relation to the bar.

6. The guide assembly of claim 5 wherein the locking member is a locking screw having a threaded portion and wherein the stud includes corresponding threads thereon to provide a threaded adjustment therebetween.

7. The guide assembly of claim 5 wherein the stud includes a channel means therethrough for slideably accepting the support bar.

8. The guide assembly of claim 7 wherein the channel means is a first channel means and wherein the stud also includes a second channel means having a different orientation from the first channel means, said second channel means for slideably accepting the post of the saw guide means.

9. The guide assembly of claim 4 wherein the saw guide means includes a substantially flat plate having a shape which substantially corresponds to at least a portion of an anterior/posterior view of a hip prosthesis and wherein the plate includes a lateral side and a medial side and wherein the post extends upwardly from the lateral side of the plate.

10. The guide assembly of claim 9 wherein the plate includes a scale for determining the relative position of the saw guide to the femur, and wherein said scale is located along said lateral side and extends up into the post.

11. The guide assembly of claim 10 wherein the scale is a first scale and wherein the plate further includes a second scale along the medial side for determining the relative position of the saw guide to the femur.

12. The guide assembly of claim 9 wherein the plate includes a main body portion and a neck portion separated from the main body portion by a cutting slot, and wherein the neck portion is attached to the main body portion by a connecting leg which extends outwardly from the medial side of the plate to interconnect the main body and neck portion.

13. The guide assembly of claim 12 wherein the neck portion of the plate includes a positioning means for corresponding with the center of the head of the femur.

14. The osteotomy guide assembly of claim 1 wherein the means for attaching the assembly to the proximal portion of the femur includes an elongated barrel which is attached to the transverse support bar, said barrel including a channel therethrough, the osteotomy guide also including an elongated intramedullary shaft means which extends partially into the medullary canal of the femur and partially protrudes from the proximal end of the femur such that the barrel of the osteotomy guide fits over the protruding portion of the intramedullary shaft means for stabilizing and locating the barrel thereon.

15. The guide assembly of claim 14 wherein the intramedullary shaft means is substantially axially aligned with the longitudinal direction of the femur and wherein the barrel, when positioned over the intramedullary shaft means, is also substantially axially aligned with the longitudinal direction of the femur, and wherein the transverse support bar extends substantially perpendicularly from the barrel.

16. The guide assembly of claim 14 wherein the barrel is slideable along the intramedullary shaft means and wherein the assembly further includes a barrel locking means to secure the barrel to the protruding portion of the intramedullary shaft means to secure the axial position of the barrel relative to the intramedullary shaft means.

17. The guide assembly of claim 16 wherein the barrel locking means includes a locking shaft member which is positioned in a locking channel which extends through a side wall of the barrel, said locking shaft member may be selectively positioned to protrude into the channel of the barrel and thus into contact with the intramedullary shaft means when the barrel is positioned over said intramedullary shaft means, to secure the barrel to the intramedullary shaft means, and wherein said locking shaft member may be selectively withdrawn out of contact with the intramedullary shaft means to release the secured positioned of the barrel relative to the intramedullary means.

18. The guide assembly of claim 17 wherein the locking channel extends through the side wall of the barrel and further extends continuously throughout the length of the support bar.

19. The guide assembly of claim 17 wherein the locking shaft member is threadably engaged in the locking channel.

20. The osteotomy guide assembly of claim 14 wherein the elongated barrel includes a first end and a second end and wherein the barrel and extending support bar form a saddle locator means for locating the guide assembly in relation to the saddle portion of the femur and wherein the saddle locator means include an angled tip at the first end of the barrel, and wherein the tip is adapted to contact the femur at the saddle portion of the femur and as such, the tip angles downwardly away from the greater trochanter of the femur when the guide assembly is attached thereto.

21. The osteotomy guide of claim 20, wherein the saddle locator means further includes an angled tip at the second end of the barrel to enable either the first end or the second end of the barrel to be placed against the saddle portion of the femur.

22. A saw guide for femoral neck osteotomy wherein the saw guide means includes a substantially flat plate having a shape which substantially corresponds to at least a portion of an anterior/posterior view of a hip prosthesis and wherein the plate includes a lateral side and a medial side and wherein the plate includes a main body portion and a neck portion separated from the main body portion by a cutting slot, and wherein the neck portion is attached to the main body portion by a connecting leg which extends outwardly from the medial side of the plate to interconnect the main body portion and neck portion and wherein the connecting leg forms an opening between the leg and main body portion and wherein the opening opens into the cutting slot.

23. The saw guide of claim 22 wherein the neck portion of the plate includes a positioning means for corresponding with the center of the head of the femur.

24. The saw guide of claim 22 wherein the guide further includes a post which extends upwardly from the lateral side of the plate and wherein the plate includes a scale for determining the relative position of the saw guide to the femur, and wherein said scale is located along said lateral side and extends up into the post.

25. The saw guide of claim 24 wherein the scale is a first scale and wherein the plate further includes a second scale along the medial side for determining the relative position of the saw guide to the femur.

26. A saw guide for femoral neck osteotomy wherein the saw guide includes a substantially flat plate and wherein the plate includes a main body portion and a further portion separated from the main body portion by a cutting slot, and wherein the further portion is attached to the main body portion by a connecting leg which extends outwardly from the plate to interconnect the main body portion and the further portion and wherein the connecting leg forms an opening between the leg and main body portion and wherein the opening opens into the cutting slot.

27. An osteotomy guide assembly for femoral neck osteotomy comprising a means for attaching the assembly to the proximal portion of a femur, a transverse support bar extending from said attachment means and a saw guide means which is attached to the support bar, and wherein the means for attaching the assembly to the proximal portion of the femur includes an elongated barrel which is attached to the transverse support bar, said barrel including a channel therethrough, the osteotomy guide also including an elongated intramedullary shaft means which extends partially into the medullary canal of the femur and partially protrudes from the proximal end of the femur such that the barrel of the osteotomy guide fits over the protruding portion of the intramedullary shaft means for stabilizing and locating the barrel thereon and wherein the elongated barrel includes a first end and a second end and wherein the barrel and extending support bar form a saddle locator means for locating the guide assembly in relation to the saddle portion of the femur and wherein the saddle locator means includes an angled tip at the first end of the barrel, and wherein the tip is adapted to contact the femur at the saddle portion of the femur and as such, the tip angles downwardly away from the greater trochanter of the femur when the guide assembly is attached thereto.

28. The osteotomy guide assembly of claim 27 wherein the saddle locator means further includes an angled tip at the second end of the barrel to enable either the first end or second end to be selectively positioned against the saddle portion of the femur.

29. The osteotomy guide assembly of claim 27 wherein the saw guide means is attached to the support bar by a locking means, and wherein said locking means provides for positional adjustment of the saw guide means relative to the support bar in at least two different linear directions.

30. A method for removal of the neck and head of a femur, comprising the steps of:
   (a) forming a longitudinal hole in the femur from the proximal end thereof that is aligned with the medullary canal of the femur;
   (b) providing an elongated intramedullary shaft which extends partially into the hole in the medullary canal and partially protrudes from the proximal end of the femur;
   (c) attaching a hollow barrel of an osteotomy guide to the protruding portion of the intramedullary shaft;
   (d) adjusting the position of a saw guide along a support bar which extends transversely from the barrel by adjusting the position in a first direction along the support bar and in second direction axially along the longitudinal direction of the femur and then securely locking this desired position of the saw guide in both directions relative to the support bar with a single locking means; and
   (e) guiding a cutting instrument against the femoral neck while the instrument is guided along a cutting surface or slot in the saw guide.

31. The method of claim 30 wherein the method further includes:
   (a) removing the barrel, support bar, and saw guide and the intramedullary shaft from the femur; and
   (b) completing the desired cutting of the neck of the femur with the cutting instrument.

* * * * *